United States Patent [19]

Lucot et al.

[11] Patent Number: 4,943,428

[45] Date of Patent: Jul. 24, 1990

[54] STIMULATION OF SEROTONIN-1A RECEPTORS IN MAMMALS TO ALLEVIATE MOTION SICKNESS AND EMESIS INDUCED BY CHEMICAL AGENTS

[75] Inventors: James B. Lucot, Xenia, Ohio; George H. Crampton, Oak Harbor, Wash.

[73] Assignee: Wright State University, Dayton, Ohio

[21] Appl. No.: 156,527

[22] Filed: Feb. 16, 1988

Related U.S. Application Data

[63] Continuation-in-part of Ser. No. 71,896, Jul. 10, 1987.

[51] Int. Cl.$^5$ .................... A61K 27/00; A61K 31/135
[52] U.S. Cl. ...................................... 424/10; 514/657; 514/872; 514/922
[58] Field of Search .................. 424/10; 514/922, 872, 514/657

[56] References Cited

U.S. PATENT DOCUMENTS

| | | | |
|---|---|---|---|
| 3,930,022 | 12/1975 | Hauck et al. | 424/330 |
| 4,076,843 | 2/1978 | Hauck et al. | 424/330 |
| 4,087,545 | 5/1978 | Archer et al. | 424/283 |
| 4,101,677 | 7/1978 | Dunnigan et al. | 424/330 |
| 4,163,063 | 7/1979 | Cannon et al. | 424/330 |
| 4,228,169 | 10/1980 | Johnson et al. | 424/258 |
| 4,410,519 | 10/1983 | Seiler et al. | 424/226 |
| 4,486,428 | 12/1984 | Eggler et al. | 424/248.4 |
| 4,620,002 | 10/1986 | Sandefur et al. | 544/230 |
| 4,680,404 | 7/1987 | Eggler et al. | 546/269 |
| 4,721,720 | 1/1988 | Wootton et al. | 514/304 |
| 4,722,933 | 2/1988 | Horn | 514/438 |
| 4,749,718 | 6/1988 | Coates et al. | 514/397 |
| 4,753,789 | 6/1988 | Tyers et al. | 424/10 |

OTHER PUBLICATIONS

Saelens, David A., Ph. D., "Antiemetic Drugs," M.U.S.C. School of Pharmacy Lecture Series, 1976, pp. 1–5.

Mansbach et al., "Discriminative Stimulus Properties of Buspirone in the Pigeon", J. Pharmacol. Exp. Ther., Feb. 1987, 240(2), pp. 364–369 (Abstract).

Goodman et al., *The Pharmacological Basis of Therapeutics*, 7th Ed (1985), pp. 633–634.

Colino et al., Chem. Abst. 106(1): 536m.

Marsden et al. Chem. Abst. 106(3): 12851y.

Allen et al., "Pharmacologic Effects of MJ9022-1, a Potential Tranquilizing Agent," Arzneim-Forsch, vol. 24(6), pp. 917–922 (1974).

James B. Lucot, "Blockade of 5-Hydroxytryptamine$_3$ Receptors Prevents Cisplatin-Induced but not Motion-or Xylazine-Induced Emesis in the Cat," Pharmacology Biochemistry & Behavior, vol. 32, pp. 207–210.

Oskenberg et al., "Antagonism of 5-Hydroxytryptamine$_{1A}$(5-HT$_{1A}$) Receptor-Mediated Modulation of Adenylate Cyclase Activity by Pindolol and Propranolol Isomers," Biochemical Pharmacology, vol. 37, No. 18, pp. 3429–3433, 1988.

Arvidsson et al., "8-Hydroxy-2-(alkylamino)tetralins and Related Compounds as Central 5-Hydroxytryptamine Receptor Agonists", J. Med. Chem., 1984, 27, 45–51.

"Communications to the Editor", Journal of Medicinal Chemistry, 1981, 24, 921–923.

Kennett et al., "Antidepressant-Like Action of 5-HT1A Agonists and Conventional Antidepressants in an Animal Model of Depression", European Journal of Pharmacology, vol. 134, pp. 265–274 (abstract).

Tricklebank et al., "Medication of the Discriminative Stimulus Properties of 8-Hydroxy-2-(di-N-propylamino) Tetralin (8-OH-DPAT) by the Putative 5-HT1A Receptor," European Journal of Pharmacology, vol. 133, pp. 47–56 (abstract).

*Primary Examiner*—Stanley J. Friedman
*Attorney, Agent, or Firm*—Killworth, Gottman, Hagan & Schaeff

[57] ABSTRACT

A method for the alleviation of both motion sickness and chemically-induced emesis is provided which includes the administration of a nontoxic, therapeutically effective amount of a composition which stimulates serotonin-1A receptors in a mammal in need of such treatment. The preferred compounds for use are buspirone and 8-hydroxy-2(di-n-propylamino)-tetralin (8-OH-DPAT).

13 Claims, 2 Drawing Sheets

STIMULATION OF SEROTONIN-1A RECEPTORS IN MAMMALS TO ALLEVIATE MOTION SICKNESS AND EMESIS INDUCED BY CHEMICAL AGENTS

BACKGROUND OF THE INVENTION

The invention described herein was made in the performance of work under NASA Contract NCC-2-229 and is subject to the provisions of 35 U.S.C. sections 200 et seq.

CROSS-REFERENCE TO RELATED APPLICATIONS

This application is a continuation-in-part of U.S. patent application Ser. No. 071,896, filed July 10, 1987.

This invention relates to a method of alleviating both motion sickness and emesis induced by chemical agents, and more particularly to the use of compositions which stimulate serotonin-1A receptors in mammals to achieve this purpose.

There are currently no known strategies or agents which are effective in blocking emesis caused from a variety of different stimuli. While some agents are effective in blocking emesis from one stimulus, the same agent may be ineffective against emesis elicited from another stimulus. For example, agents which are known to be effective in blocking motion sickness have not been found to be effective against emesis which is induced chemically. Moreover, even agents having such limited effectiveness such as antihistamines and antimuscarinics may produce undesirable sedative side effects.

This ineffectiveness of known antiemetic agents against a variety of stimuli is believed to be due to the fact that workers in the art have determined that different neural pathways are responsible for chemically-induced vomiting than for motion-induced emesis. See, Brand and Perry, "Drugs Used In Motion Sickness", 18 Pharmacol. Rev. 895–924 (1966). For example, the drug xylazine stimulates alpha-2 noradrenergic receptors in the area postrema, also known as the chemical trigger zone, in the brain. Cisplatin, a cytotoxic drug compound used in cancer chemotherapy, triggers emetic effects by activating nerves passing through or close to the area postrema.

Ablation of the area postrema eliminates emesis elicited by xylazine and cisplatin compounds. See, Colby et al, "Emetic Action of Xylazine on the Chemoreceptor Trigger Zone for Vomiting in Cats", 4 J. Vet. Pharmacol. Therap. 9396 (1981) and McCarthy and Borison, "Cisplatin-induced Vomiting Eliminated by Ablation of the Area Postrema in Cats", 68 Cancer Treat. Rep. 401–404 (1984). The mechanism for motion-induced emesis, however, uses a neural pathway that does not require the area postrema. Ablation of the area postrema does not eliminate motion-induced emesis. Borison and Borison, "Motion Sickness Reflex Arc Bypasses the Area postrema in Cats", 92 Exp. Neurol. 723–737 (1986).

Similarly, while the drug yohimbine blocks xylazine-induced emesis, it does not block motion sickness. Lucot and Crampton, "Xylazine Emesis, Yohimbine, and Motion Sickness Susceptibility in the Cat", 237 Pharmacol. Exp. Therap. 450–455 (1986). Also, while the drug scopolamine blocks motion sickness, it does not prevent xylazine-induced emesis.

It would be desirable to find a drug or class of drugs which effectively alleviate motion sickness but do not exhibit the sedative effects of presently used agents. It would also be desirable to find a drug or class of drugs which are also effective in blocking chemically induced emesis from a variety of stimuli. Accordingly, there is still a need in the art for a drug or class of drugs which will alleviate or block motion sickness and/or chemically induced emesis but which do not exhibit sedative effects on the patient.

SUMMARY OF THE INVENTION

The present invention meets that need by providing a class of agents for the alleviation of motion sickness as well as chemically induced emesis in mammals which do not have the sedative side effects of other agents presently in use. In accordance with one aspect of the present invention, a mammal in need of treatment for motion sickness or chemically induced emesis is administered a nontoxic, therapeutically effective amount of a composition which stimulates serotonin-1A receptors in a mammal in need of such treatment. Examples of preferred serotonin-1A stimulators include 8-hydroxy-2(di-n-propylamino)-tetralin, also known as 8-OH-DPAT, and buspirone. An anticipated preferred dose is approximately 0.002 to about 4.0 mg/kg of body weight, with dosage being dependent upon a number of factors including the species of mammal, the mammal's susceptibility to emetic stimuli, and the nature of the stimulus.

The preferred serotonin-1A stimulating compounds are from two different drug classes and appear to share the effect of stimulating serotonin-1A receptors in a mammal to block both motion and chemically induced emesis. Because different stimuli induce emesis through different neural pathways, applicants believe that the site of the serotonin-1A receptors must be at a convergent structure in the brain, presumably at or very near the somewhat ill-defined vomiting center. This center is believed to program the complex series of reflexive responses that constitutes the emetic sequence. While both of the preferred serotonin-1A stimulating agents also exhibit antianxiety action, other well-known antianxiety agents have not been found to possess this broad-spectrumed antiemetic effect.

Accordingly, it is an object of the present invention to provide a method for the alleviation of motion sickness and/or chemically induced emesis in a mammal in need of treatment by the administration of an agent which does not have the sedative effects of other previously used agents. This, and other objects and advantages of the invention will become apparent from the following detailed description, the accompanying drawing figures, and the appended claims.

DESCRIPTION OF THE PREFERRED EMBODIMENTS

Figure 1:
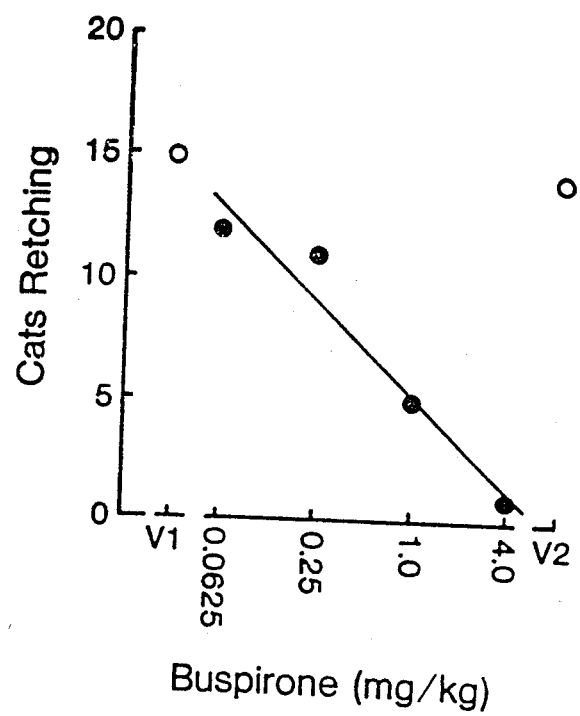
FIG. 1 graphically illustrates the dosage dependent reduction of motion sickness in twenty cats by the administration of buspirone. Control tests following saline treatment alone were made both before (V1) and after (V2) the determination of the dose response function.

The process of the present invention utilizes a class of compositions which act as stimulators for serotonin-1A sites in the brains of mammals. These sites are believed to be at or near the vomiting center in the brain stem, the point at which the complex series of reflexive responses constituting the emetic sequence is programmed. The activity of this class of compositions, at the convergent vomiting center, makes them useful in treating and alleviating emetic responses to a wide variety of emetic stimuli, including both motion and chemical sources.

In this art, cats are recognized as suitable test animals with test results being correlatable with utility in humans. Like humans, some cats are more susceptible to motion sickness than others. The cerebrospinal fluid of cats that had become motion sick was studied. It was determined that the cerebrospinal fluid of those cats had lower baseline levels of 5-hydroxyindolacetic acid than the fluid of cats not becoming motion sick. Accordingly, it would appear that nerves using serotonin as a transmitter substance may be involved in the emetic process. Applicants believe that this lower activity in serotogenic systems of cats which are more susceptible permits motion sickness and possibly other emetic syndromes to develop.

The preferred compounds for use in the practice of the process of the present invention are known. While they are from different chemical classes, they share the common property of stimulating serotonin-1A receptors. One of the preferred compounds is the pyrimidine compound, better known as buspirone, or a pharmaceutically acceptable acid addition salt thereof. Buspirone has the following structural formula:

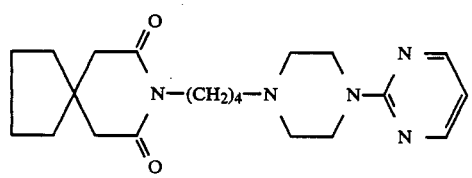

The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN). See, 225 J. Amer. Med. Assn. 520 (1973).

The synthesis of the compound and the identification of its properties are described in the following patents and publications:

1. Wu et al., 15 J. Med. Chem. 477 (1972). "Psychosedative Agents. 2. 8-(4-Substituted 1-piperazinylalkyl)-8-azaspiro[4.5]decane-7,9-diones";

2. Wu et al., U.S. Pat. No. 3,717,634, issued Feb. 20, 1973, entitled "N-(Heteroarcyclic)piperazinylalkylazaspiroalkanediones";

3. Allen et al., Arzneim.-Forsch. 24, Nr. 6, 917-22(1974). "Pharmacologic Effects of MJ 9022-1, a Potential Tranquilizing Agent";

4. Sathananthan et al., 18 Therapeutic Research 701-05(1975). "MJ 9022: Correlation Between Neuroleptic Potential and Stereotypy"; and 5. Wu et al., U.S. Pat. No. 3,976,776, issued Aug. 24, 1976, entitled "Tranquilizer Process Employing N-(Heteroarcyclic)piperazinylalkylazaspiroalkanediones".

In recent years, buspirone has found use in a number of different clinical methods. For example, Casten et al., U.S. Pat. No. 4,182,763, issued Jan. 8, 1980, teaches that buspirone is useful as an anti-anxiety agent in the treatment of psychiatric disorders. Kurtz et al., U.S. Pat. No. 4,634,703, issued Jan. 6, 1987, teaches that buspirone is useful in the treatment of panic disorders.

Allen et al., U.S. Pat. No. 4,438,119, issued Mar. 20, 1984, teaches that buspirone alleviates extrapyramidal motor disorders such as Parkinson's disease. Finally, Othmer et al., U.S. Pat. No. 4,640,921, issued Feb. 3, 1987, teaches that buspirone may be used to treat sexual dysfunction. While buspirone has found an increasing number of uses in recent years, to applicants' knowledge, it has never been used to attempt to alleviate motion sickness in mammals.

Buspirone is known to be a partial agonist at 5-hydroxytryptamine$_{1A}$ receptors, where it binds with sixteen times greater affinity than at dopamine receptors. Buspirone preferentially antagonizes presynaptic dopamine$_2$ receptors, so that it not only mimics 5-hydroxytryptamine transmission, but also, at higher doses, increases dopaminergic transmission. See, Andrade and Nicoll, "The Novel Anxiolytic Buspirone Elicits a Small Hyperpolarization and Reduces Serotonin Responses on Hippocampal CAI pyramidal Cells", Soc. Neurosci. Abstr. 11, 597 (1985); McMillan, Matthews, Sanghera, Shepard and German, "Dopamine Receptor Antagonism by the Novel Antianxiety Drug, Buspirone", J. Neurosci. 3, 733-738 (1983): and Peroutka, "Selective Interaction of Novel Anxiolytics with 5-Hydroxytryptamine-1A Receptors", Biol. Psychiat. 20, 971-979 (1985). As buspirone acts to stimulate a subtype of serotonin receptor known as the serotonin-1A site, applicants have found that the use of buspirone in this manner in mammals having a susceptibility to motion sickness counteracts the lower serotogenic and/or dopaminergic activities and blocks or otherwise alleviates the symptoms of motion sickness.

Further, applicants have also found that buspirone is effective in blocking chemically-induced emesis in cats, the chemical xylazine is a known agent which induces emesis. Treatment with buspirone prior to exposure to xylazine acts to block the action of that chemical agent. While the exact mechanism by which buspirone blocks emesis is not known, applicants believe that buspirone acts at the convergent vomiting center in its stimulation of serotonin-1A receptor sites. This conclusion is partially based on the fact that buspirone is inactive at muscarinic and histaminergic receptors where current agents known to be effective against motion sickness acts. Buspirone is also inactive at alpha-2 adrenoceptors where xylazine acts to induce emesis. Because buspirone blocks emesis elicited by both motion and chemical stimuli, it has been found to be useful against an even broader spectrum of emetic agents including the cytotoxic drug cisplatin (a cis-platinum compound) used in chemotherapy and is believed to be useful against gastric irritants such as copper sulfate.

The other preferred compound used in the practice of the present invention is the naphthalene compound 8-hydroxy-2(di-n-propylamino)-tetralin, sometimes referred to as 8-OH-DPAT. 8-OH-DPAT has the following structural formula:

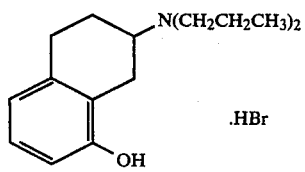

8-OH-DPAT is known to have antidepressant and anxiolytic effects on mammals. See, Kennett et al, "Antidepressant-like Action of 5-HT1A Agonists and Conventional Antidepressants in an Animal Model of Depression", 134 Europ. J. Pharmacol. 265–274 (1987) and Tricklebank et al, "Mediation of the Discriminative Stimulus Properties of 8-hydroxy-2(di-n-propylamino)-tetralin (8-OH-DPAT) by the Putative-HT1A Receptor", 133 Europ. J. Pharmacol. 47–56 (1987). As 8-OH-DPAT, like buspirone, acts to stimulate serotonin-1A sites, applicants have found that the use of 8-OH-DPAT in accordance with the practice of the present invention blocks or otherwise alleviates both the symptoms of motion sickness as well as emesis induced by chemical agents.

In order that the invention may be more readily understood, reference is made to the following examples, which are intended to illustrate the invention, but are not to be taken as limiting the scope thereof.

EXAMPLE 1

Twenty mature female cats with normal righting and post-rotational nystagmic reflexes but which were susceptible to a well characterized motion stimulus were selected for testing. The basis for selection was that the cats vomited on at least one of the five screening tests.

The screening tests were conducted on a motion stimulus device which resembles an amusement park Ferris wheel ride. The cats rode in clear plastic boxes suspended from 0.445 meter arms that were rotated at 0.28 Hz. Motion tests were of 30 minutes duration followed by one minute of observation at rest. Further detail concerning the motion stimulus is reported by Crampton and Lucot,"A Stimulator for Laboratory Studies of Motion Sickness in Cats", 56 Aviat. Space Environ. Med. 462-65(1985), the disclosure of which is hereby incorporated by reference.

411 tests were separated by two weeks to prevent habituation to the motion stimulus. The dependent variable was retching, which was followed by vomiting in all cases. Freshly prepared buspirone hydrochloride was injected s.c. (subcutaneously) in a volume of 0.1 ml/kg thirty minutes before exposure to the motion stimulus. All doses were of the base. Saline control tests were conducted before (V1) and after (V2) determination of the dose responsive curve.

The administration of buspirone clearly blocked motion sickness as shown by the results illustrated in FIG. 1. The $ED_{50}$ was 0.41 mg/kg of body weight as computed by probit analysis. There was no significant change in the susceptibility of the cats during the course of the testing as shown by the incidence of retching on control tests before and after determination of the dose responsive curve. There was a correlation of 0.58 ($P<0.01$) the minimum effective dose of buspirone against motion sickness and the susceptibility to motion sickness as measured by the percentage of tests during which retching occurred on the five previous screening tests. This indicates that the more susceptible the animal is to motion sickness, the greater the premedication dosage required to suppress retching.

EXAMPLE 2

Buspirone was also found to be effective in blocking chemically induced emesis. In this test, fifteen female cats were used, none of which were included in the motion sickness tests reported above. The animals were injected s.c. with 0.66 mg/kg of xylazine base in a volume of 0.066 ml/kg, placed in a clear plexiglass enclosure, and observed for 30 minutes or until the first retch. Seven days later, the cats received 4.0 mg/kg of body weight buspirone base s.c. thirty minutes before s.c. administration of 0.66 mg/kg of xylazine. Seven days thereafter, the cats received an s.c. administration of 0.66 mg/kg of xylazine.

As shown in Table I, the incidence of retching was reduced significantly by pretreating the cats with buspirone compared to the incidence on the pre- and post-xylazine challenges (one tail binomial test). The higher dosage levels of buspirone to block this chemically induced emesis is believed to be related to the more provocative stimulus of xylazine as an emetic agent as compared to motion as a stimulus. Following the administration of the higher doses of buspirone, the cats were more difficult to handle and exhibited strong defensive behavior. This behavior persisted to a lessening degree during handling and injections for several weeks thereafter.

TABLE 1

Effects of pretreatment with 4.0 mg/kg buspirone base on the incidence of retching induced by 0.66 mg/kg xylazine administered 30 min. later.

| Condition | No. retching/ No. tested |
| --- | --- |
| Pre-test: | |
| xylazine alone | 11/15 |
| Buspirone: | |
| then xylazine | 5/15[a] |
| Post-test: | |
| xylazine alone | 14/15[b] |

[a]Significantly different from the pre- and post-tests by $p<0.05$ and $p<0.002$ respectively
[b]Not significantly different from the pre-test

EXAMPLE 3

A control and an experimental group were each assigned six cats, four male and two female. Jugular catheters were implanted unilaterally under ketamine and pentobarbital anesthesia and sterile conditions. Each catheter was implanted on the jugular, threaded under the skin and externalized through a stab wound in the back of the neck. Catheter patency was maintained by withdrawing blood, flushing with 50 U/ml heparin immediately following surgery and every other day thereafter.

Experiments were conducted 72-96 hours after implantation. Cats in both experimental and control groups received intravenous infusions over a period of 4-5 minutes of 7.5 mg/kg cisplatin (cis-platinum II diamine dichloride from Sigma Chemical Co., St. Louis, Mo.). This dose has been established as the most reliable for eliciting emesis in the cat. See McCarthy and Borison, "Cisplatin-induced Vomiting Eliminated by Ablation of the Area Postrema in Cats", Cancer Treat. Rep. 68:401–404 (1984).

Buspirone (Buspar® from Bristol-Myers Co., Evansville, Ind.) was administered subcutaneously to the cats in the experimental group immediately before cisplatin infusion. The dose was 4 mg/kg base and was dissolved in sterile saline in a concentration of 40 mg/ml. The number and latency of emetic events (retching and vomiting) were recorded over the following six hours. The cats were euthanized by intravenous infusions of T-61® (Hoechst, Somerville, N.J.) at the end of the observation period.

Buspirone was effective in preventing cisplatin-induced emesis as shown by the results report in Table II. The number of cats that received buspirone and vomited was lower than the number that were not pretreated and vomited (Fisher's Exact Test; $p<0.05$). The number of emetic events as well as the latency to the first emesis were also significantly different (Wilcoxin's test; $p<0.05$). The cats sat quietly in the test cage during the observation and appeared normal.

TABLE II

Effects of buspirone on cisplatin-induced emesis

| CONTROL | | | BUSPIRONE | | |
|---|---|---|---|---|---|
| Cat | Emetic Events | Latency to first emesis | Cat | Emetic Events | Latency to first emesis |
| 488 | 1 | 72:45[1] | 494 | 0 | <360[2] |
| 489 | 2 | 171:35 | 517 | 0 | <360 |
| 491 | 6 | 71:47 | 505 | 0 | <360 |
| 500 | 0 | >360 | 495 | 1 | 214:17 |
| 497 | 9 | 47:51 | 499 | 0 | <360 |
| 421 | 6 | 95:37 | 506 | 0 | <360 |

[1]Minutes:Seconds
[2]No emesis during observation period

EXAMPLE 4

Twenty mature female cats with normal free-fall righting and vestibulo-ocular reflexes but which were susceptible to a well characterized motion stimulus were selected for testing for both motion sickness and xylazine trials using 8-OH-DPAT. The basis for selection was that the cats vomited on at least one of the five screening tests. Another ten female cats which were not susceptible to motion sickness were selected and assigned to the group of cats being tested in the xylazine challenge group.

Twenty-four male and female cats were selected and assigned to the group of cats being tested in the cisplatin challenge. A few of the females were tested for motion sickness and found to be not susceptible; the male cats were not tested for susceptibility to motion sickness. In the control group were four males and six females. In the group receiving the low dose were three males and five females. In the group receiving the high dose were two males and four females.

EMETIC CHALLENGES AND RESULTS

A. Motion Stimulus. The screening tests were conducted on a motion stimulus device which resembles an amusement park Ferris wheel ride. The cats rode in clear plastic boxes suspended from 0.445 meter arms that were rotated at 0.28 Hz (17 rpm). Motion tests were minutes duration followed by one minute of observation at rest. Further detail concerning the motion stimulus is described in Example 1.

411 tests were separated by two weeks to prevent habituation to the motion stimulus. The dependent variable was retching, which was followed by vomiting in all cases. Saline control tests were conducted before and after every determination of a dose responsive curve.

8-OH-DPAT (Research Biochemicals Inc., Wayland, Mass.) was dissolved in a sterile saline solution to an injection volume of 0.01 ml/kg of body weight. The order of doses was 0.04, 0.01, 0.002, and 0.02 mg/kg, respectively. The 8-OH-DPAT was administered subcutaneously 15 minutes before the cat was exposed to the motion stimulus.

Figure 2:
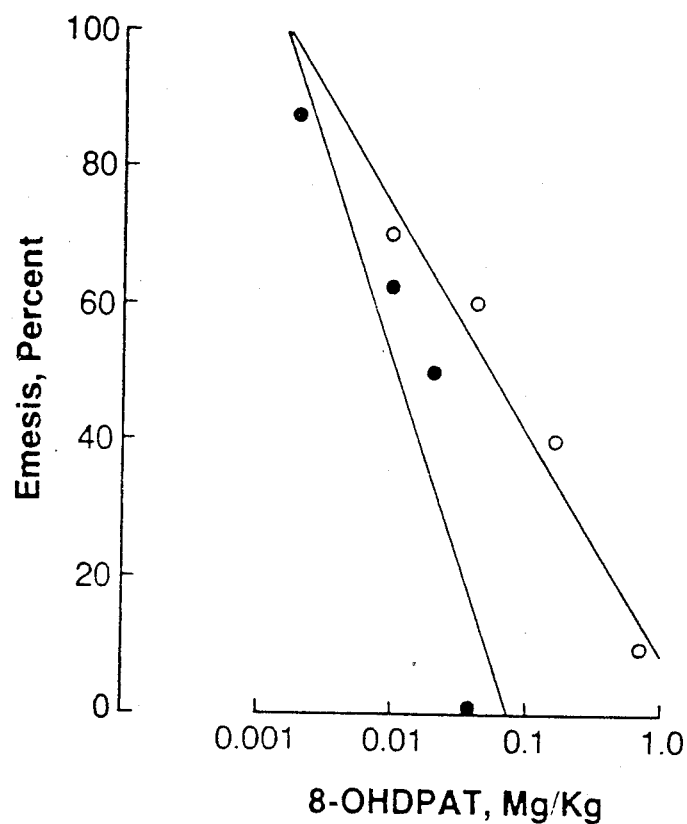
FIG. 2 graphically illustrates the dosage dependent reduction of both motion sickness (solid circles) and xylazine-induced emesis (open circles) in ten cats by the administration of 8-hydroxy-2(di-n-propylamino)-tetralin. The log of the dose of 8-OH-DPAT is presented.

As shown in FIG. 2, 8-OH-DPAT produced a dosage dependent decrease in the incidence of motion sickness (solid circles) (Fisher-Yates test; $P<0.01$). There was no change in the susceptibility of the cats as demonstrated by the absence of change in the pre- and post-drug vehicle tests in which eight of the ten cats became motion sick in both tests. The $ED_{50}$ was 0.011 mg/kg of body weight. The line of best fit (dose responsive curve expressed as the log dose of the number of moles) was not different from parallel to the line describing the buspirone dose responsive curve in FIG. 1. 8-OH-DPAT was approximately 25 times more potent than buspirone in alleviating motion sickness.

B. Xylazine. Xylazine HCL (Bayvet, Shawnee, Kans.) was dissolved in sterile saline solution to an injection volume of 0.066 ml/kg of body weight. The compound was then administered subcutaneously, and the cats were monitored for thirty minutes or for fifteen minutes after the emetic event, whichever occurred later. Saline was administered before the xylazine challenge both before and after determination of a dose responsive curve for the antiemetic compound 8-OH-DPAT to verify that xylazine was an effective emetic stimulus.

In addition, saline solution alone was administered between determinations of dose responsive curves for the antiemetic compounds to evaluate conditioned responses to the injection procedure. Xylazine tests were conducted at weekly intervals. As in the motion challenge, 8-OH-DPAT was dissolved in sterile saline solution to an injection volume of 0.1 ml/kg. The order of doses was 0.01, 0.04, 0.16, and 0.64 mg/kg. 8-OH-DPAT was administered subcutaneously 15 minutes before the administration of xylazine.

8-OH-DPAT also produced a dose-dependent decrease in xylazine-induced emesis (Fisher-Yates test; $p<0.01$) as illustrated by FIG. 2 (open circles). There was no change in the efficacy of xylazine, with all ten cats vomiting to the administration of xylazine alone both before and after determination of the 8-OH-DPAT dose-responsive curve. The $ED_{50}$ was 0.056 mg/kg of body weight.

The dose-responsive curves for the effects of 8-OH-DPAT on motion sickness and xylazine-induced emesis were not different from parallel. When compared to the effects of buspirone on xylazine-induced emesis above, 8-OH-DPAT was approximately 16 times more potent. The highest dose of 0.64 mg/kg produced strong defensive behavior in the cats similar to the behavior reported for buspirone above. However, unlike buspirone, the effect was not evident on the following day.

C. Cisplatin. Jugular catheters were implanted under sterile conditions and ketamine and pentobarbital anesthesia as in Example 3. Antibiotics were administered after the surgery. The catheters were implanted in the jugular vein, threaded under the skin, and externalized at the nape of the neck. Catheter patency was maintained by withdrawing blood, flushing with 50 U/ml heparin and filling with 1000 U/ml heparin. This was done immediately after surgery and every other day thereafter. The heparin was withdrawn just prior to the infusion of cisplatin. Experiments were conducted 72-96 hours after implantation.

Cisplatin (Sigma Chemical Co., St. Louis, Mo.) was prepared by placing it into a solution of 2 mg/ml in sterile water by gentle warming and sonicating. Both the experimental and control groups received intravenous infusions of cisplatin over a period of 4-5 minutes. The challenge dose of 7.5 mg/kg was chosen as in Example 3.

In the experimental group, 8-OH-DPAT was administered subcutaneously immediately before the cisplatin infusion. The dose of 0.16 mg/kg was initially chosen because it produced acute and residual changes in behavior, and its effects on xylazine-induced emesis were approximately equivalent to that of 4.0 mg/kg of buspirone. The number and latency of emetic events (retching and vomiting) were observed for six hours after the infusion. At the end of the observation period, the cats were euthanized by intravenous administration of T-61 ® (Hoechst, Somerville, N.J.).

As shown by Table III, 8-OH-DPAT produced a decrease in cisplatin-induced emesis. The dose of 0.16 mg/kg produced an increased latency to the first emetic event that was not significant, and failed to alter significantly the number of emetic events. The dose of 0.64 mg/kg significantly decreased the number of events ($P<0.05$) and significantly altered the latency to the first event. Neither dose produced significant effects by the Fisher-Yates test. As compared to the effects of buspirone on cisplatin-induced emesis, 8-OH-DPAT was approximately four times more potent.

TABLE III

| Control latency$^a$/no.$^b$ | 0.16 mg/kg dose latency/no. | 0.64 mg/kg dose latency/no. |
|---|---|---|
| 47.85/9 | 61.35/12 | 49.15/1 |
| 51.81/6 | 100.55/6 | 285.97/1 |
| 71.78/6 | 102.67/5 | 360.00/0 |
| 72.75/1 | 171.83/3 | 360.00/0 |
| 87.65/3 | 360.00/0 | 360.00/0 |
| 95.62/6 | 360.00/0 | 360.00/0 |
| 96.90/4 | 360.00/0 | 360.00/0 |
| 171.58/2 | 360.00/0 | 360.00/0 |
| 360.00/0 | 360.00/0 | 360.00/0 |

$^a$Latency to the first emetic event in minutes; 360 denotes a test with no emesis.
$^b$Number of emetic events.

EXAMPLE 5

The cats tested in Example 4 above were also tested for the possibility that the known anti-anxiety effects of both buspirone and 8-OH-DPAT could be responsible for the antiemetic effects which were observed. Known antianxiety agents such as barbiturates have been reported to alleviate motion sickness in dogs, while benzodiazepines have been reported to alleviate the emesis associated with cancer chemotherapy in humans.

With respect to xylazine-induced emesis, lorazepam (Sigma Chemical Co., St. Louis, Mo.), a benzodiazepine compound having known anti-anxiety and sedative effects, failed to have any effect even though lorazepam has been reported to alleviate emesis in humans induced by cancer chemotherapy. The lorazepam was prepared by suspending it in sterile saline solution with one drop of Tween-80 per five ml by sonication in hot water. The PH was adjusted to 7.0 with sodium hydroxide. The injection volume was 0.5 ml/kg. pretreatment with doses of 0.1 and 0.4 mg/kg of lorazepam resulted in all ten tested cats vomiting when xylazine was administered.

With respect to motion sickness. Pretreatment with 0.1 mg/kg of lorazepam decreased the number of cats becoming motion sick from eight to five, which was not considered significant by either McNemar's test or by Wilcoxin's test as applied to the latency to emesis. Higher doses were not tested because the cats were drowsy and ataxic at this dose. Observations during xylazine testing using a dose of 0.4 mg/kg lorazepam established that the higher dose produced pronounced ataxia and gross nonspecific behavior observable even the following day. These effects were considered toxic, and the motion group of cats was not subjected to the higher lorazepam dosage level.

The results show that the nonspecific factors associated with relief from anxiety do not account for the antiemetic effects observed. Doses of lorazepam sufficient to produce pronounced nonspecific effects in the cats tested still did not affect the response to both motion-induced and xylazine-induced emesis.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A method for the alleviation of motion sickness, which comprises administering a nontoxic, therapeutically effective dose of 8-hydroxy-2(di-n-propylamino)-tetralin to a mammal in need of such treatment.

2. The method of claim 1 in which the dosage of 8-hydroxy-2(di-n propylamino)-tetralin is from about 0.002 to about 0.64 mg/kg of body weight.

3. The method of claim 1 in which the dosage of 8-hydroxy-2(di-n-propylamino)-tetralin is about 0.011 mg/kg of body weight.

4. A method for the alleviation of chemically induced emesis which comprises administering a nontoxic, therapeutically effective dose of 8-hydroxy-2(di-n-propylamino)-tetralin to a mammal in need of such treatment.

5. The method of claim 4 in which the emesis was induced by a cis-platin compound.

6. The method of claim 5 in which the dosage of 8-hydroxy-2(di-n-propylamino)-tetralin is from about 0.16 to about 0.64 mg/kg of body weight.

7. The method of claim 4 in which the emesis was induced by xylazine.

8. The method of claim 7 in which the dosage of 8-hydroxy-2(di-n-propylamino)-tetralin is from about 0.01 to about 0.64 mg/kg of body weight.

9. The method of claim 7 in which the dosage of 8-hydroxy-2(di-n-propylamino)-tetralin is about 0.056 mg/kg.

10. A method for the alleviation of motion sickness which comprises administering a nontoxic, therapeutically effective dose of a composition which stimulates serotonin-1A receptors in a mammal in need of such treatment.

11. A method for the alleviation of chemically induced emesis which comprises administering a nontoxic, therapeutically effective dose of a composition which stimulates serotonin-1A receptors in a mammal in need of such treatment.

12. A method for the alleviation of emesis induced by the chemical agents cis-platin compounds, xylazine, and copper sulfate which comprises administering a non-toxic, therapeutically effective dose of 8-hydroxy-2(di-n-propylamino)-tetralin to a mammal in need of such treatment.

13. A method for the alleviation of emesis induced by the chemical agents cis-platin compounds, xylazine, and copper sulfate which comprises administering a non-toxic, therapeutically effective dose of a composition which stimulates serotonin-1A receptors in a mammal in need of such treatment.

* * * * *